United States Patent [19]

Chiapetta et al.

[11] Patent Number: 4,751,190

[45] Date of Patent: Jun. 14, 1988

[54] FLUORESCENCE POLARIZATION IMMUNOASSAY AND REAGENTS FOR USE THEREIN

[75] Inventors: Enrico G. Chiapetta, Mundelein; Robert J. Kucera, Lindenhurst, both of Ill.

[73] Assignee: Abbott Laboratories, North Chicago, Ill.

[21] Appl. No.: 847,801

[22] Filed: Apr. 3, 1986

Related U.S. Application Data

[63] Continuation-in-part of Ser. No. 757,822, Jul. 22, 1985, abandoned.

[51] Int. Cl.$^4$ ............... G01N 33/533; G01N 33/536; G01N 33/542
[52] U.S. Cl. .................................. 436/546; 436/501; 436/536; 436/537; 436/800; 436/805; 436/825; 436/826
[58] Field of Search ............... 436/546, 800, 536, 537, 436/825, 826, 501, 805; 252/126

[56] References Cited

U.S. PATENT DOCUMENTS

| | | | |
|---|---|---|---|
| 3,864,317 | 2/1975 | Ogata et al. | 525/353 |
| 3,873,721 | 3/1975 | Hargett | 514/547 |
| 4,119,401 | 10/1978 | Sansur et al. | 436/97 |
| 4,492,762 | 1/1985 | Wang et al. | 436/536 |

FOREIGN PATENT DOCUMENTS

| | | | |
|---|---|---|---|
| 2323605 | 5/1973 | Fed. Rep. of Germany | 252/126 |
| 8600933 | 2/1986 | PCT Int'l Appl. | |

OTHER PUBLICATIONS

Chemical Abstracts, 103:68 (1985).
Modern Fluorescence Spectroscopy 3, New York, Plenum Press, 1981, pp. 167-174.

*Primary Examiner*—Esther M. Kepplinger
*Assistant Examiner*—Stephen C. Wieder
*Attorney, Agent, or Firm*—Robert W. Stevenson; Martin L. Katz

[57] ABSTRACT

An method of carrying out a fluorescence polarization immunoassay is disclosed wherein the immunoassay is conducted in the presence of from about 0.001 to about 1.0 percent (weight/volume) of dioctyl sodium sulfosuccinate. Also disclosed are reagents useful in the practice of the immunoassay method.

3 Claims, No Drawings

FLUORESCENCE POLARIZATION IMMUNOASSAY AND REAGENTS FOR USE THEREIN

BACKGROUND OF THE INVENTION

This application is a continuation-in-part of U.S. patent application Ser. No. 757,822, filed July 22, 1985, now abandoned.

TECHNICAL FIELD

The present invention relates generally to a method, and reagents useful in the method, for determining ligands in liquids, especially biological fluids such as serum, plasma, spinal fluid, amnionic fluid and urine. The present invention relates more particularly to novel fluorescence polarization immunoassays which employ dioctyl sodium sulfosuccinate as a surfactant to improve the performance of the assay.

BACKGROUND ART

Competitive binding immunoassays for measuring ligands are well known, and are based on the competition between a ligand in a test sample and a labeled reagent, referred to as a tracer, for a limited number of receptor binding sites on antibodies specific to the ligand and tracer. The concentration of ligand in the sample determines the amount of tracer that will specifically bind to an antibody. The amount of tracer-antibody complex produced can be quantitatively measured and is inversely proportional to the quantity of ligand in the test sample.

Fluorescence polarization immunoassay techniques are based on the principle that a fluorescent labeled compound when excited by plane polarized light, will emit fluorescence having a degree of polarization inversely related to its rate of rotation. Specifically, when a molecule such as a tracer-antibody complex having a fluorescent label is excited with plane polarized light, the emitted light remains highly polarized because the fluorophore is constrained from rotating between the time when light is absorbed and when it is emitted. When a "free" tracer compound (i.e., unbound to an antibody) is excited by plane polarized light, its rotation is much faster than that of the corresponding tracer-antibody complex; therefore, the emitted light is depolarized to a much greater extent. Thus, the molecular rotational relaxation time, and hence the magnitude of the fluorescence polarization response, is directly related to the molecular size of the compound. Accordingly, when plane polarized light is passed through a solution containing a relatively high molecular weight fluorescent compound, the degree of polarization of the emitted light will in general be greater than when plane polarized light is passed through a solution containing a low molecular weight fluorescent compound. Thus, fluorescence polarization provides a quantitative means for measuring the amount of tracer-antibody complex produced in a competitive binding immunoassay.

The fluorescence polarization principle is ordinarily utilized in an assay by mixing a sample containing an analyte or ligand of interest (or suspected of containing an analyte) with a "tracer", i.e., a labelled compound similar to the analyte but capable of producing a fluorescence polarization response to plane polarized light. Conventionally, the analyte or ligand is a relatively low molecular weight compound, i.e. less than about 2,000 daltons, but the analyte may be substantially larger, e.g., having a molicular weight on the order of 100,000 daltons or more, as long as it is capable of measurement using fluorescent polarization immunoassay techniques (see, for example, co-pending U.S. application Ser. No. 757,822 filed July 22, 1985, the disclosure of which is incorporated herein by reference, which describes a fluorescent polarization immunoassay for C-reactive protein having a molecular weight of about 120,000 daltons). Antibody specific to the analyte and the tracer is also included in the mixture. The tracer and the ligand compete for a limited number of receptor binding sites on the antibody. The amount of tracer that will bind is inversely related to the concentration of analyte in the sample, since the analyte and tracer each bind to the antibody in proportion to their respective concentrations.

The TDx@ Fluorescence Polarization Analyzer, an instrument commercially available from Abbott Laboratories, Abbott Park, Ill., is an automated system for the performance, inter alia, of fluorescence polarization assays. The TDx@ Analyzer has achieved remarkable commercial success in providing fluorescent polarization immunoassays to clinical laboratories for the determination in patient samples of many ligands, including antiasthmatic drugs, such as theophylline, antiarrhythmic drugs, such as lidocaine, N-acetylprocainamide, procainamide and quinidine, antibiotic drugs, such as amikacin, gentamicin, kanamycin, netilmicin, streptomycin, tobramycin and vancomycin, anticonvulsant drugs, such as carbamazepine, phenytoin, phenobarbital, primidone, and valproic acid, antineoplastic drugs, such as methotrexate, cardiac glycosides, such as digoxin, thyroid function assays, such as T-uptake and thyroxine, and others. The TDx@ Analyzer and its use in the performance of immunoassays is described in Jolley, et al., "Fluorescence Polarization Immunoassay I. Monitoring Aminoglycoside Antibiotics in Serum and Plasma", *Clinical Chemistry* 27/7. 1190–1197 (1981); Popelka, et al., "Fluorescence Polarization Immunoassay II. Analyzer for Rapid, Precise Measurement of Fluorescence Polarization with Use of Disposable Cuvettes", *Clinical Chemistry* 27/7, 1198–1201 (1981); Jolley, et al., "Fluorescence Polarization Immunoassay III. An Automated System for Therapeutic Drug Determination", *Clinical Chemistry* 27/9, 1575–1579 (1981); and Lu-Steffes, et al., "Fluorescence Polarization Immunoassay IV. Determination of Phenytoin and Phenobarbital in Human Serum and plasma", *Clinical Chemistry* 28/11, 2278–2282 (1982).

One problem encountered in the use of fluorescent polarization immunoassay techniques to determine analytes of interest in serum or plasma samples is background fluorescence present in varying degrees in the samples. Icteric serum or plasma can contribute a significant error to the desired polarization measurement. A major fluorescent component of icteric serum or plasma is albumin-bound bilirubin. Bilirubin is the final product of heme catabolism and in normal individuals is present in serum at less than 1 mg/dl. In various disease states affecting the liver, bilirubin is markedly elevated, reaching 10–20 mg/dl in some cases. Neonates ofter attain high levels in the 10–20 mg/dl range due to poor liver function immediately post-partum. Bilirubin is relatively nonfluorescent when it is in aqueous solution, but becomes highly fluorescent if bound to albumin (Chen, *Arch. Biochem. Biophys.* 160, 106–112) and bilirubin-albumin binding is very tight (Gray, et al., *J. Biol.*

*Chem.* 253, 4370–4377). Therefore, serum or plasma samples with elevated bilirubin levels will exhibit an elevated fluorescence due to the presence of the bilirubin-albumin complex.

In order to avoid erroneous results due to background fluorescence, a blank reading is usually taken on a serum or plasma sample in the TDx Analyzer prior to performance of an assay, which is then subtracted from the final assay reading to arrive at a corrected value. However, background subtraction may be ineffective to adequately compensate for background fluorescence in some elevated bilirubin samples, and degredation of the bilirubin-albumin complex during the course of the assay can result in inaccurate compensation for background fluorescence in such samples. Accordingly, U.S. Pat. No. 4,492,762 discloses conducting fluorescent polarization immunoassays in a solution containing effective amounts of an anionic surfactant to disrupt bilirubin-serum albumin complex in the sample and thereby reduce background fluorescence of the sample. The '762 patent discloses that a broad category of anionic surfactants are useful for this purpose and that concentration ranges of 0.001 to 0.2 (weight/volume) percent are preferred. Preferred surfactants for use in the practice of the method of the '762 patent have been sodium dodecyl sulfate and sodium cholate. Although the method of the '762 patent has proven to be highly effective in limiting measurement errors on the TDx. Analyzer due to elevated bilirubin levels in serum samples, the use of such surfactants has precluded the development of fluorescence assays for some ligands, such as where sensitivity requirements and large sample volumes are needed due to low concentrations of the ligand in the sample being tested. In these cases, the use of sodium dodecyl sulfate or other surfactants disclosed in the '762 patent would require sufficiently high levels of surfactant as to result in antibody or analyte degredation in the performance of the assay. In order to overcome this problem for low concentrations of relatively low molecular weight ligands, such as therapeutic drugs like digoxin, a harsh pretreament step has been required to remove bilirubin interference in fluorescence polarization immunoassays, for example by denaturing proteins in the serum. For low concentrations of relatively large molecules, such as proteins, such pretreatments can not be used since they would result in denaturation of the analyte in the sample, and fluorescence polarization immunoassays for such relatively large molecules using fluorescence polarization techniques has not been possible. These and other problems with prior art systems are overcome by the practice of the present invention wherein fluoresence polarization immunoassays for analytes in serum or plasma samples are conducted in the presence of dioctyl sodium sulfosuccinate.

SUMMARY OF THE INVENTION

In the practice of the present invention, dioctyl sodium sulfonate ("DSS") is employed as an anionic surfactant in fluorescence polarization immunoassays to reduce background resulting from bilirubin-serum albumin complex in serum samples. It has been unexpectantly found that dioctyl sodium sulfonate is highly effective for this purpose at relatively low concentrations with little or no degredation effect on antibody employed in the assay, thereby permitting the use of fluorescence polarization techniques to determine the concentration of analytes heretofore precluded by prior art methods.

The invention further encompasses certain novel reagents useful in the above-described method.

DETAILED DESCRIPTION OF THE INVENTION

Definitions

DSS or dioctyl sodium sulfonate as used herein is the compound sulfobutanedioic acid 1,4-bis(2-ethylhexyl)ester sodium salt having the structural formula:

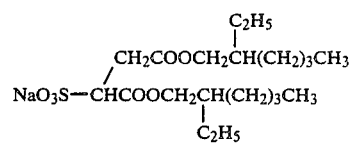

In addition to the sodium salt, other salts, such as the potassium salt, calcium salt, lithium salt, magnesium salt and other equivalent salts, are included within the scope of the invention as set forth herein.

The term "ligand", as used herein, refers to a molecule such as a hapten, to which a binding protein, such as a receptor or an antibody, can be obtained or formed. Such haptens are protein-free compounds, generally of low molecular weight, which do not induce antibody formation when injected into an animal, but which are reactive to antibodies. In addition, the term "ligand" may refer to a moderate to high molecular weight compounds such as proteins, e.g., C-reactive protein. Antibodies to haptens are generally raised by first conjugating the haptens to a protein and injecting the conjugate product into an animal. The resulting antibodies are isolated by conventional, well-known antibody isolation techniques.

The term "ligand-analog", as used herein, refers to a mono- or polyvalent radical, a substantial portion of which has the same spatial and polar organization as the ligand to define one or more determinant or epitopic sites capable of competing with the ligand for the binding sites of a receptor. A characteristic of such ligand-analog is that it possesses sufficient structural similarity to the ligand of interest so as to be recognized by the antibody for the ligand. For the most part, the ligand-analog will have the same or substantially the same structure and charge distribution (spatial and polar organization) as the ligand of interest (for purposes of the present invention, CRP) for a significant portion of the molecular surface. Since frequently, the linking site for a hapten will be the same in preparing the antigen for production of antibodies as that used in the tracer for linking to the ligand, the same portion of the ligand analog which provides the template for the antibody will be exposed by the ligand analog in the tracer.

The present invention involves the use of fluorescein and derivatives of fluorescein. In particular, a necessary property of fluorescein and its derivatives for the usefulness of the tracer compounds is the fluorescence of fluorescein. These compounds provide the fluorescent response when excited by polarized light of an appropriate wavelength, thereby to enable the fluorescence polarization measurement to be made. Generally, the tracer compounds used in the assay provided by the present invention are formed of conjugates of the ligand to be determined, or a ligand-analog, with fluorescein or a fluorescein derivative, and exist in solution as biologically acceptable salts such as sodium, potassium, ammonium and the like, which allows the compounds to exist in the open, fluorescent form, when employed in the analytical methods of the present invention. The specific salt present depends on the buffer employed to adjust the pH level, for example, in the presence of a sodium phosphate buffer, the compounds utilized in the present invention will generally exist in the open form, as a sodium salt. Suitable fluorescein tracer compounds for use in the invention include, for example, carboxyfluorescence fluorescein isothiocynates (FITC), triazinylaminofluoresceins (DTAF) and many other compounds well kown in the art, including those disclosed in the art previously cited. The selection of a particular fluoerescent tracer for use is a matter of choice for the routine, given the teachings hereof, and is not crucial to the practice of the present invention.

Fluorescence Polarization Immunoassay

In accordance with the method of the present invention, a sample containing a ligand to be determined is intermixed with a tracer and an antibody specific for the ligand and the tracer in the presence of DSS. Concentration ranges of DSS in the reaction mixture effective in the practice of the invention will depend on the specific ligand, antibody and other reagents employed in the assay, but will generally be in the range of about 0.001 to about 1.0 percent (weight/volume), more preferably about 0.002 to about 0.5 percent (weight-/volume) and most preferably about 0.005 to about 0.1 percent (weight/volume). The ligand present in the sample and the tracer compete for a limited number of antibody sites, resulting in the formation of ligand-antibody and tracer-antibody complexes. By maintaining constant the concentration of tracer and antibody, the ratio of ligand-antibody complex to tracer-antibody complex that is formed is directly proportional to the amount of ligand present in the sample. Therefore, upon exciting the mixture with polarized light and measuring the polarization of the fluorescence emitted by a tracer and a tracer-antibody complex, one is able quantitatively to determine the amount of ligand in the sample.

A tracer in solution which is not complexed to an antibody is free to rotate in less than the time required for absorption, and re-emitted light is relatively randomly oriented so that the fluorescence polarization of a tracer not complexed to an antibody is low, approaching zero. Upon complexing with a specific antibody, the tracer-antibody complex thus formed assumes the rotation of the antibody molecule which is slower than that of the relatively small tracer molecule, thereby increasing the polarization observed. Therefore, when a ligand competes with the tracer for antibody sites, the observed polarization of fluorescence of the resulting mixture of the free tracer and tracer-antibody complex assumes a value intermediate between that of the tracer and that of the tracer-antibody complex. If a sample contains a high concentration of the ligand the observed polarization value is closer to that of the free ligand, i.e., low. If the test sample contains a low concentration of the ligand, the polarization value is closer to that of the bound ligand, i.e., high. By sequentially exciting the reaction mixture of an immunoassay with vertically and then horizontally polarized light and analyzing only the vertically polarized component of the emitted light, the polarization of fluorescence in the reaction mixture can be accurately determined. The precise relationship between polarization and concentration of the ligand to be determined is established by measuring the polarization values of calibrators with known concentrations. The concentration of the ligand can be interpolated from a standard curve prepared in this manner.

The pH at which the method of the present invention is practiced must be sufficient to allow the tracers to exist in their ionized state. The pH maY range from about 3 to 12, more usually in the range of from about 5 to 10, most preferably from about 6 to 9. Various buffers can be used to achieve and maintain the pH during the assay procedure. Representative buffers include borate, acetate, phosphate, carbonate, tris, barbital and the like. The particular buffer employed is not critical to the present invention, but in an individual assay, a specific buffer may be preferred in view of the antibody employed and ligand to be determined. The cation portion of the buffer will generally determine the cation portion of the tracer salt in solution.

The methods of the present invention are practiced at moderate temperatures and preferably at a constant temperature. The temperature will normally range from about zero degrees to about 50 degrees C., more usually from about 15 degrees to about 40 degrees C.

The concentration of ligand which can be assayed in accordance with the invention will generally vary from about $10^{-2}$ to about $10^{-13}$M, more usually from about $10^{-4}$ to about $10^{-10}$M. High concentrations of ligand can be assayed upon dilution of the original sample.

In addition to the concentration range of ligand, considerations such as whether the assay is qualitative, semiquantitative or quantitative, the equipment employed, and the characteristics of the tracer and antibody will normally determine the concentration of the tracer and antibody which is used. While the concentration range of ligand in the sample will determine the range of concentration of the other reagents, i.e., tracer and antibody, normally to optimize the sensitivity of the assay, individual reagent concentrations will be determined empirically. Appropriate concentrations of the tracer and antibody are readily ascertained by one of ordinary skill in the art.

Although not forming part of the present invention, it is to be appreciated that the fluorescence polarization immunoassay for ligands provided by the present invention can be performed especially advantageously using reagents and assay procedures, in accordance with the invention, on a TDx (registered trademark) Fluorescence Polarization Analyzer, commercially available from Abbott Laboratories, Abbott Park, Ill., from whom full details concerning operation and features of this Analyzer are available.

The present invention also contemplates a reagent for use in the assays of the invention, which, upon dilution in the performance of the assay, will result in a DSS concentration in the reaction mixture within the concentration ranges heretofore described. The concentration of DSS in the reagent will vary depending on the assay protocol for which it is intended to be used, but will advantageously comprise from about 0.01 to about 20.0 percent (weight/volume) DSS, more preferably about 0.02 to about 15.0 percent (weight/volume) DSS and most preferably about 0.05 to about 10.0 percent (weight/volume) DSS. The solvent system of the reagent of the invention may be an aqueous solvent or an organic solvent which is miscible in water, such as one or more of ethylene glycol, propylene glycol, DMSO, DMF, lower alkanols or the like. One presently particularly preferred solvent system is a mixture of 2-propanol, DMSO and propylene glycol. The reagent comprising DSS will preferably be a pretreatment buffer solution for use in the assay.

EXAMPLES

The following examples describe experiments which were performed in accordance with the concepts of the present invention, and are directed to assays for CRP and T3 using fluorescence polarization techniques. Although examples are illustrated herein for these ligands, which present significant technical difficulties using prior art anionic surfactants, it is to be understood that the inventive concepts are equally applicable to assays for other ligands as described herein. Such assays can be conducted in accordance with the following general procedure:

(1) A measured volume of standard or test serum is delivered into a test tube and diluted with a pretreatment buffer comprising DSS;

(2) A known concentration of antisera is added to the tubes;

(3) A known concentration of a tracer optionally containing a surfactant is then added to each tube;

(4) The reaction mixture is incubated at room temperature; and (5) The amount of tracer bound to antibody is measured by fluorescence polarization techniques as a measure of the amount of ligand in the sample.

Although the principles of the invention fully are applicable to non-automated assays, the automated nature of TDx assays assures minimal technician time to perform assays or interpret data.

EXAMPLE 1

Automated C-Reactive Protein Assay by Fluorescence Polarization Immunoassay

Isolation of Human C-Reactive Protein

CRP is obtained from malignant ascitic and pleural fluids by calcium-dependent affinity chromatography on pneumococcal C-polysaccharide covalently coupled by cyanogen bromide-activated Sepharose. It is then gel filtered on Ultrogel AcA44 (acrylamide-agarose beads) in the presence of calcium ions, combining molecular sieve chromatography with removal of contaminating SAP by its affinity for agarose. Residual trace contaminants are removed by immunoabsorption with anti-normal human serum and anti-SAP antibodies insolubilised on Sepharose and by absorption with Sepharose-Con A to remove glycoproteins and Blue-Sepharose to remove albumin. After a final gel filtration step on Sephacryl S-300, between 35–40% of the initial CRP is recovered in substantially pure form.

CRP Antisera Production

Sheep and goats are immunized by deep subcutaneous or intramuscular injections of isolated CRP emulsified in complete Freund's adjuvant, followed by bi-weekly or monthly booster injections of emulsions in incomplete adjuvant. Each injection contains at least 500 microgramns CRP. This regiment is followed for all animals for a five month period while the animals are monitored for antibody titer at biweekly or monthly bleeding intervals. Booster injections are then interrupted for three months while titer monitoring continued. Following the three months rest, boosting is resumed as titers begin to drop.

Tracer Synthesis DTAF/CRP

A stock solution of 5-(4,6-dichloro-triazin-2-yl)-Amino Fluorescein, (DTAF) is prepared in absolute ethanol with the aid of sonification, at 2 mg/ml. Stock CRP contains in 0.005 Molar Borate buffer, pH 9.0, 0.002 Molar $CaCL_2$ and 0.9% NaCl at 3 mg/ml, is made to a concentration of 500 micrograms in 0.04 Molar Borate buffer pH 9.0, 0.002M $CaCl_2$, 0.9% NaCl. To 1 ml of the (500 micrograms/ml) CRP solution, 25 microliters of stock DTAF is added. The coupling reaction is then carried out for 1 hour at ambient temperature with mixing, in the dark. At the end of the 1 hour period, the DTAF reaction is quenched with 50 ul of 10% glycine prepared in 0.04 Molar borate buffer, pH 9.0 (same buffer as above), and incubated with mixing for 15 minutes at the above conditions. The conjugate is chromatographed over sephodex G-25 and eluted with Borate buffer pH 9.0 (same buffer as above) and collected at void volume. It is then diluted to a desired concentration for use in an automated assay on the TDx Analyzer.

Automated C-Reactive Protein Assay Reagents, Calibrators and Controls

Tracer: The stock DTAF/CRP conjugate is diluted in buffer containing protein and salt stabilizers and 0.1% $NaN_3$ as preservative, to give a net intensity reading of 3000 at gain of 20 on the TDx Analyzer.

Antiserum: Dilutions of raw CRP antiserum are made at from 1:10 to 1:100. 25 ul of each dilution is added to a cuvette and allowed to incubate with 25 ul of tracer reagent in 2 ml final volume of 0.1M Phosphate buffer, pH 7.5, 0.01% Bovine-gamma ethylene glyco-Globulin (BGG), 0.1% $NaN_3$ and 2% (by Volume). The antiserum and tracer react for 3.4 minutes at 35° C. in the above buffered conditions. A dilution factor is determined for the antiserum which is based on the fluorescence polarization measured. The antiserum reagent is then prepared in the above phosphate buffer by diluting the raw antiserum according to the determined dilution factor.

Pretreatment: Pretreatment buffer reagent consists of a solution of 3.5% (weight/volume) DSS in 0.05 Molar Tris, pH 8.0, 0.1% $NaN_3$ as preservative and other organic stabilizing solvents.

Buffer: TDx assay buffer consists of 0.1 Molar Phosphate, pH 7.5, 0.01% Bovine-gamms-Globulin (BGG) and 0.1% $NaN_3$ as a preservative.

Calibrators: C-Reactive protein is placed in buffered synthetic serum matrix containing protein and salt stabilizers and 0.1% $NaN_3$ as a preservative.

Controls: (Contained in the same matrix as calibrators)

Stabilizing Media Reagent Composition For DTAF/CRP Tracer

| Constituent | Concentration grams/liter | Other |
| --- | --- | --- |
| Tris | 12.11 | (0.1 Molar) |
| $Na_2SO_4$ (Anhydrous) | 20.0 | (2%) |
| Ovalbumin Hydrolysate | 5.0 | (0.5%) |
| Propylene Glycol | 20.0 ml | (2% by volume) |
| $CaCl_2\ 2H_2O$ | 0.294 | (0.002 Molar) |

| Constituent | Concentration grams/liter | Other |
|---|---|---|
| NaN$_3$ | 1.0 | (0.1%) |

Adjust pH with: 6 N HCl to 7.0

Acceptable variations of the above formula:
pH range 6–8
Na$_2$SO$_4$ concentration at 4% and 0.2% Ovalbumin at pH 7.0
Substitute 2% Ethylene glycol for 2% Propylene glycol
Substitute Na$_2$SO$_4$ with (NH$_4$)$_2$SO$_4$, Oval bumin Hydrolysate with ovalbumin.

The above formulation is found to stabilize the CRP-DTAF conjugate for 10 days at 45° C.

Stabilizing Media Reagent Composition for Calibrators/Controls.

| Constituent | Concentration grams/liter | Other |
|---|---|---|
| Tris | 12.11 | (0.1 Molar) |
| Na$_2$SO$_4$ | 8.0 | (8.0%) |
| Ovalbumin Hydrolysate | 10.0 | (1.0%) |
| CaCl$_2$ 2H$_2$O | 0.294 | (0.002 Molar) |
| NaN$_3$ | 1.0 | (0.1%) |

The pH is adjusted with 6 N HCl to pH 8.0.

The above formulation has been found to stabilize C-Revitive protein for 30 days at 45° C.

Pretreatment Reagent Composition

| Constituent | Concentration | grams or milliliter/liter |
|---|---|---|
| Tris | 0.05 Molar | 6.06 g |
| NaN$_3$ | 0.1% | 1.00 g |
| 2-Propanol | 10% by Volume | 100.0 ml |
| DMSO | 25% by Volume | 200.0 ml |
| Propylene Glycol | 5% by Volume | 20.0 ml |
| Dioctyl Sodium Sulfosuccinate at 60% Stock Concentration | 4% | 66.67 ml |

The pH is adjusted to 8.0 with 6N HCl. This pretreatment composition has been found to be effective in eliminating Bilirubin interference at Bilirubin concentrations of 20 mg/dl while using a CRP assay sample volume of 8.0 microliters.

Assay Procedure

A fluorescence polarization immunoassay (FPIA) for CRP is carried out on the TDx Fluorescense Polarization Analyzer as follows. The reaction sequence, incubation, timing, reagent volumes and sample volumes are microprocessor controlled according to programmed assay parameters. To perform the CRP assay, specimens and reagents are loaded on the TDx Analyzer, in their respective receptacles. Specimen, antiserum, pretreatment reagent and buffer are dispensed into the reaction well. One-half of the final volume of the diluted specimen is dispensed into the cuvette along with sufficient buffer to give one-half the final reaction volume. A background intensity reading is taken on the mixture of specimen, antiserum and pretreatment reagent. The second half of the diluted specimen is dispensed into the cuvette with tracer and buffer to provide the final reaction volume of 2 ml. The final intensity measurement is then made. The specific assay sequence for performing the TDx/CRP procedure comprises the following steps:

1. 8.6 microliter of specimen are dispensed into the reaction well, and 25 microliters of buffer are added.
2. 10 microliters of pretreatment reagent and 25 microliters of antiserum reagent are added to the specimen in the reaction well and 431.4 microliters of buffer are added to bring the final reaction well volume to 500 microliters.
3. An additional 25 microliters of pretreatment reagent are dispensed to the cuvette.
4. 174 microliters of the specimen, antiserum and pretreatment mixture contained in the reaction well is transferred to the cuvette, and diluted with 776 microliters of buffer, to obtain an intermediate cuvette colume of 1000 microliters.

Note: Steps 1–4 are repeated for each sample and are accomplished in 18.4 seconds per sample.

5. The cuvette contents are incubated for 6.4 minutes at 34° C. while a background reading is taken at 3.4 minutes and stored for each specimen.
6. Following the background recording, an additional 174 microliters of specimen, antiserum and pretreatment reagent mixture is transferred from the reaction well to the cuvette and 20 microliters of buffer are added.
7. 25 microliters of tracer reagent are added to the cuvette and sufficient buffer added (601 microliters) to give a final cuvette colume of 2 ml.
8. The final cuvette reaction mixture is incubated for 3.4 minutes and a final reading taken for each specimen.
9. The blank reading is subtracted from the final reading and net polarization reading is reported for each specimen.
10. The net polarization reading is converted to a CRP concentration by utilizing four stored mathematical constants derived from a calibration curve, previously generated with calibrators of known CRP concentration. The four constants are determined by a least-square curve-fit four parameter program which is part of the date-handling system associated with the TDx Analzyer.

Utilizing the assay performed according to the invention, as previously described, recovery of CRP added to a specimen containing normal levels of CRP to give approximate concentrations of 2, 10 and 20 mg/dl CRP is 100%, 100% and 99.6%, respectively. To two other samples containing slightly elevated levels of CRP, an approximate concentration of 10 mg/dl is added. The recovery from these samples was 98.9% and 97.4%. Results are summarized below.

| Initial Sample CRP Conc. mg/dl | Concentrated CRP Added mg/dl | Measured CRP Conc. mg/dl | % Recovery |
|---|---|---|---|
| .15 | 2.19 | 2.34 | 100 |
| .15 | 10.96 | 11.11 | 100 |
| .15 | 21.92 | 21.99 | 99.6 |
| 1.73 | 9.55 | 11.17 | 98.9 |
| 1.68 | 9.55 | 10.98 | 97.4 |

Effect of DSS on Bilirubin-Albumin Complex

Background:

A stock solution of bilirubin (Sigma Chemical Co., Cat. No. B40126) is prepared at 1000 mg/dl in 0.1M NaOH. The stock solution is used to spike low (L), medium (M) and high (H) CRP-containing standard serum samples to obtain bilirubin concentrations in the samples as set forth below. The samples are then assayed according to the foregoing procedure using (a) the pretreatment reagent composition comprising DSS previously described, or (b) the pretreatment reagent composition previously described but comprising 0.7% sodium dodecyl sulfate (SDS) and 0.5% lauryl dodecyl sulfate (LDS) in place of DSS. The percentage bilirubin interference for each assay is determined according to the following equation:

$$\% \text{ Interference} = \frac{[CRP_B] - [CRP_C]}{[CRP_C]} \times 100$$

where $[CRP_B]$ is the measured concentration of CRP in a bilirubin-containing sample and $[CRP_C]$ is the measured concentration of CRP in a corresponding control without bilirubin. The results are as follows:

| Bilirubin Conc. mg/dl | CRP Level Tested | SDS/LDS % Interference | DSS % Interference |
|---|---|---|---|
| 4.8 | L | 17.1 | 4.8 |
| | M | 4.3 | −0.8 |
| | H | 8.3 | 0.9 |
| 9.8 | L | 30.9 | −4.9 |
| | M | 5.6 | −2.1 |
| | H | 11.1 | 3.5 |
| 14.8 | L | 41.5 | 2.8 |
| | M | 7.2 | 1.9 |
| | H | 12.2 | 1.9 |
| 20.3 | L | 100+ | 6.1 |
| | M | 9.6 | −0.4 |
| | H | 18.8 | 4.1 |
| 24.6 | L | 100+ | 18.1 |
| | M | 7.3 | 4.8 |
| | H | 18.0 | 7.9 |

Correlation with other methods:

Human serum specimens are obtained for a period of one and one-half months from a patient population requested for CRP testing. A CRP value for each specimen is generated at the hospital utilizing a commercial nephelometric method. Samples are transported frozen, then tested by the CRP assay as aforedescribed. Patient results from both methods are compared by linear regression analysis. The following results are indicated for the 345 specimens tested:

Correlation Coefficient = 0.992
Slope = 0.976
y-intercept = 3.0 micrograms/ml

A field study was conducted at a local hospital for approximately two weeks. During this period seventy clinical specimens were tested, using three methods: Nephelomethy (NPM), radialimmunodiffusion (RID) and the assay according to the invention as previously described (TDx CRP). Correlation data from the three methods as summarized below.

| Method Compared | Slope | Intercept | r |
|---|---|---|---|
| TDx CRP vs. NPM CRP | 1.06 | −0.17 | 0.99 |
| TDx CRP vs. RID CRP | 0.97 | 0.40 | 0.99 |
| NPM CRP vs. RID CRP | 0.91 | 0.50 | 0.98 |

Assay Sensitivity

A detection limit of 0.3 mg/dl was based on two standard derivatives taken away from the millipolarization (mP) mean of twenty "zero" calibrator replicates. The resulting mP was then read of the calibration curve found to correspond to a CRP concentration of 0.3 mg/dl.

$X_{20} = 270.55$ mP
Std. Dev. = 0.529 mP
Std. Dev.'s. = 1.06 mP = 0.3 mg/dl

It is apparent that various modifications and variations that can be made by one skilled in the art from the specific disclosure of the invention herein contained, without departing from the spirit and scope of the invention, as defined solely in the following claims.

What is claimed is:

1. In a method of determining the presence or amount of a ligand in a sample by fluorescence polarization immunoassay comprising adding a tracer and an antibody specific for said ligand and observing a polarization value as an indication of the amount of ligand in the sample the improvement comprising: conducting the fluorescent polarization immunoassay in the presence of from about 0.001 to about 1.0 percent (weight/volume) of dioctyl sodium sulfosuccinate.

2. The method of claim 1 wherein the fluorescence polarization immunoassay is conducted in the presence of about 0.002 to about 0.5 percent (weight/volume) of dioctyl sodium sulfosuccinate.

3. The method of claim 1 wherein the fluorescence polarization immunoassay is conducted in the presence of about 0.005 to about 0.1 percent so dioctyl sodium sulfosuccinate.

* * * * *